(12) United States Patent
Kurdyumov

(10) Patent No.: US 8,932,616 B2
(45) Date of Patent: Jan. 13, 2015

(54) HYDROPHOBIC POLYSACCHARIDES WITH SILYL ETHER LINKAGES HAVING ENHANCED DEGRADATION AND MEDICAL ARTICLES MADE THEREFROM

(75) Inventor: Aleksey V. Kurdyumov, Maplewood, MN (US)

(73) Assignee: Surmodics, Inc., Eden Prairie, MN (US)

( * ) Notice: Subject to any disclaimer, the term of this patent is extended or adjusted under 35 U.S.C. 154(b) by 293 days.

(21) Appl. No.: 12/894,929

(22) Filed: Sep. 30, 2010

(65) Prior Publication Data

US 2011/0076314 A1  Mar. 31, 2011

Related U.S. Application Data

(60) Provisional application No. 61/247,402, filed on Sep. 30, 2009.

(51) Int. Cl.
| | |
|---|---|
| A61F 13/00 | (2006.01) |
| A61L 29/04 | (2006.01) |
| A61L 15/28 | (2006.01) |
| A61L 27/20 | (2006.01) |
| A61L 31/04 | (2006.01) |

(52) U.S. Cl.
CPC ............... *A61L 29/043* (2013.01); *A61L 15/28* (2013.01); *A61L 27/20* (2013.01); *A61L 31/042* (2013.01)
USPC .......... 424/422; 424/488; 514/58; 536/123.12

(58) Field of Classification Search
None
See application file for complete search history.

(56) References Cited

U.S. PATENT DOCUMENTS

| | | | |
|---|---|---|---|
| 4,011,392 A | 3/1977 | Rudolph et al. | |
| 5,459,258 A | 10/1995 | Merrill et al. | |
| 5,470,581 A | 11/1995 | Grillo et al. | |
| 5,869,647 A | 2/1999 | Narayan et al. | |
| 6,007,614 A | 12/1999 | Billmers et al. | |
| 6,528,642 B1 | 3/2003 | Duval et al. | |
| 6,562,961 B1 * | 5/2003 | Seeger et al. | 536/56 |
| 7,192,484 B2 | 3/2007 | Chappa et al. | |
| 7,919,111 B2 | 4/2011 | Chudzik et al. | |
| 2002/0058763 A1 | 5/2002 | Duval | |
| 2002/0123624 A1 | 9/2002 | Qiao et al. | |
| 2003/0215649 A1 | 11/2003 | Jelle | |
| 2004/0037886 A1 | 2/2004 | Hsu | |
| 2004/0208985 A1 | 10/2004 | Rowan et al. | |
| 2005/0019371 A1 | 1/2005 | Anderson et al. | |
| 2005/0255142 A1 | 11/2005 | Chudzik et al. | |
| 2006/0249705 A1 | 11/2006 | Wang et al. | |
| 2007/0065481 A1 | 3/2007 | Chudzik et al. | |
| 2007/0087025 A1 | 4/2007 | Fitzhugh et al. | |
| 2007/0218102 A1 * | 9/2007 | Chudzik et al. | 424/426 |
| 2007/0224247 A1 | 9/2007 | Chudzik et al. | |
| 2007/0260054 A1 | 11/2007 | Chudzik | |
| 2010/0093662 A1 | 4/2010 | Defaye et al. | |
| 2010/0099861 A1 | 4/2010 | Okamoto et al. | |
| 2010/0303879 A1 | 12/2010 | Kurdyumov et al. | |
| 2010/0316687 A1 | 12/2010 | Swan et al. | |
| 2011/0076314 A1 | 3/2011 | Kurdyumov | |
| 2011/0076337 A1 | 3/2011 | Slager et al. | |
| 2011/0159067 A1 | 6/2011 | Rolfes Meyering | |
| 2011/0159101 A1 | 6/2011 | Kurdyumov et al. | |

FOREIGN PATENT DOCUMENTS

| | | |
|---|---|---|
| EP | 0 405 917 | 1/1991 |
| JP | 2001/321094 | 3/2001 |
| WO | 02/094224 | 11/2002 |
| WO | 2008/009831 | 1/2008 |
| WO | 2008/136512 | 11/2008 |

OTHER PUBLICATIONS

PCT Search Report for International Application No. PCT/US2010/050871; mailed on Feb. 24, 2011.
Péan, et al. (1999) *Why Does PEG 400 Co-Encapsulation Improve NGF Stability and Release from PLGA Biodegradable Microspheres?* Pharmaceutical Research 16: 1294-1299.
Varela, et al., (2005) *Evaluation of biochemical analytes in vitreous humor collected after death in West Indian manatees*, JAVMA 226: 88-92.
Chen, et al., (1995) *Enzymatic and chemoenzymatic approaches to synthesis of sugar-based polymer and hydrogels*, Carbohydrate Polymers 28: 15-21.
van Veen, et al. (2005) *The Effect of powder blend and tablet structure on drug release mechanisms of hydrophobic starch acetate matrix tablets*, European Journal of Pharmaceutics and Biopharmaceutics 61: 149-157.
Tarvainen, et al. (2004) *Aqueous starch acetate dispersion as a novel coating material for controlled release products*, Journal of Controlled Release 96: 179-191.
Magdassi, et al. (2001) *Interfacial Properties of Hydrophobically Modified Biomolecules: Fundamental Aspects and Applications*, J. Dispersion Science and Technology. 22: 313-322.
Na, et al. (2003) *Self-assembled nanoparticles of hydrophobically-modified polysaccharide bearing vitamin H as a targeted anti-cancer drug delivery system*, European Journal of Pharmaceutical Sciences 18: 165-173.

(Continued)

*Primary Examiner* — Suzanne Ziska
(74) *Attorney, Agent, or Firm* — Kagan Binder, PLLC

(57) ABSTRACT

Hydrophobic α(1→4)glucopyranose polymers with enhanced degradation properties are described. Between the α(1→4)glucopyranose polymeric portion and the hydrophobic portion exists a linker portion having a silyl ether chemistry that facilitates degradation of the polymer. Biodegradable matrices can be formed from these polymers, and the matrices can be used for the preparation of implantable and injectable medical devices wherein the matrix is capable of degrading in vivo at an increased rate. Matrices including and capable of releasing a bioactive agent in vivo are also described.

23 Claims, No Drawings

(56) References Cited

OTHER PUBLICATIONS

Uekama, K. (2004) *Pharmaceutical Application of Cyclodextrins as Multi-functional Drug Carriers,* Yakugaku Zasshi 124: 909-935.

Kaur, et al. (2004) *Role of Cyclodextrins in Ophthalmics,* Current Drug Delivery 1: 351-360.

* cited by examiner

HYDROPHOBIC POLYSACCHARIDES WITH SILYL ETHER LINKAGES HAVING ENHANCED DEGRADATION AND MEDICAL ARTICLES MADE THEREFROM

PRIORITY CLAIM

This application claims the benefit of U.S. Provisional Patent Application Ser. No. 61/247,402 filed Sep. 30, 2009 entitled HYDROPHOBIC POLYSACCHARIDES WITH SILYL ETHER LINKAGES HAVING ENHANCED DEGRADATION, the disclosure of which is incorporated herein by reference.

TECHNICAL FIELD

The present invention relates to hydrophobic derivatives of polysaccharides, and articles including these derivatives for use within the body.

BACKGROUND

Biodegradable polymers have been used to prepare biodegradable polymeric matrices that can be associated with, or formed into, implantable medical devices. For example, biodegradable polymers can be used to make a thin coating on a medical device's surface, generally designed to enhance the function of the device. Biodegradable polymers having thermoplastic properties can even be molded or formed into a shape to provide an implantable device having a structural property useful for treating a medical condition at the site of implantation. In theory, the polymeric matrix becomes totally degraded in the body. This can be advantageous for various medical applications, for example, such as to eliminate the requirement for explantation of the implanted article.

Implantable articles formed of or associated with biodegradable polymeric matrices can also be used to modulate the delivery of drugs to a patient at the site of implantation. Drug-releasing biodegradable matrices can be in the form of a coating on a device, or in the form of an implantable or injectable article that is formed primarily of the biodegradable polymer. Drug contained within the biodegradable matrix can be released or eluted from the matrix after the article has been introduced into the body.

Although there is a considerable amount of information regarding the use of biodegradable polymers for implantable medical devices, this field remains very technically challenging from a number of standpoints. For example, although biodegradable polymers should have properties suitable for the formation of a polymeric matrix in a desired form (such as a coating or a microparticle) it is often difficult to prepare such forms using conventional biodegradable polymers.

Also, the biodegradable polymeric matrix should be biocompatible, as well as the products that it degrades into. The polymeric matrix should not elicit a body response that adversely affects its intended function, such as a negative tissue response (e.g., a prolonged inflammatory response) at the site of implantation. Poly(lactide) and poly(glycolide) have considerable use as biodegradable polymers for implantable devices, but there are concerns regarding the amount of acidic degradation products generated upon their hydrolysis.

Another challenge relates to the actual biodegradability of the matrix that is implanted or injected in the body. Although many biodegradable polymers exhibit biodegradability in in vitro systems, they may not degrade in matrix form after the matrix has been introduced into the body. In other words, the chemical or physical property of the matrix may obstruct chemical or enzymatic activity required for degradation of the polymer (degradation that is otherwise seen when the polymer is free in solution and subjected to these degrading chemical or enzymatic activities). Accordingly, a lack of biodegradability of the polymeric matrix can diminish or negate the intended function of the device.

Also, some matrices degrade by bulk erosion. Bulk erosion may result in the loss of portions of the matrix after implantation and may cause an embolic event. In systems designed to release a drug, bulk erosion may result in loss of control over the drug release from the matrix.

SUMMARY OF THE INVENTION

Generally, the present invention relates to hydrophobic derivatives of natural biodegradable polysaccharides. The invention also relates to polymeric matrices formed from these polymers, articles including these polymeric matrices, and methods for using these matrices, such as for the treatment of a medical condition. The hydrophobic derivatives of natural biodegradable polysaccharides have chemistries that promote increased degradation of matrices formed from these polymers.

In one aspect, the invention provides a hydrophobic α(1→4)glucopyranose polymer which includes a poly-α(1→4)glucopyranose portion comprising glucopyranose monomeric units and groups that are pendent from the poly-α(1→4)glucopyranose portion. The pendent groups include one or more hydrocarbon group(s). Collectively, the hydrocarbon groups represent the hydrophobic portion of the hydrophobic α(1→4)glucopyranose polymer, which are present in an amount sufficient to make the polymer hydrophobic. In a pendent group, between the one or more hydrocarbon group(s) and the glucopyranose monomeric unit is a linker segment that includes a silyl ether group.

The presence of a silyl ether group in the linker segment enhances the rate of degradation of compositions or matrices that are formed from the hydrophobic α(1→4)glucopyranose polymer and overcomes difficulties with biodegradable matrices that display insufficient rates of degradation.

In some aspects, the hydrophobic α(1→4)glucopyranose polymer has a pendent group including silyl ether segment and one or more hydrocarbon group(s) according to formula I:

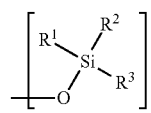

In formula I, one or more of $R^1$, $R^2$, and/or $R^3$ comprise a $C_1$-$C_{18}$ hydrocarbon group, with the proviso that the total number of carbon atoms in $R^1$, $R^2$, and/or $R^3$ is at least three.

Optionally, and in addition to pendent groups including a silyl ether segment, the hydrophobic α(1→4)glucopyranose polymer can include one or more additional pendent group(s) comprising a hydrophobic group which is linked to the poly-α(1→4)glucopyranose portion via a linker segment that is different than the silyl ether segment.

As a general matter, biodegradable polymeric matrices or compositions can be formed from these inventive hydrophobic α(1→4)glucopyranose polymers having the silyl ether linker chemistries. The matrices can be in various forms. These forms include microparticles, a coated layer on a device surface, non-solidified droplets, or a three-dimensional implant. In some cases, the matrices can be associated with an implantable article, which can be fabricated from a material that is different that the biodegradable polymers of the invention.

Therefore, in some aspects, the invention provides an implantable or injectable biomedical article, the article comprising a polymeric matrix or composition formed of hydrophobic α(1→4)glucopyranose polymers having pendent groups which include one or more hydrocarbon groups and a linker segment that includes a silyl ether group.

Articles prepared from or associated with polymeric matrices formed from the hydrophobic α(1→4)glucopyranose polymers can be introduced into the body. The matrices or compositions can be placed or formed at a target location in a subject (i.e., in vivo). After a period of time, the polymer can degrade, resulting in erosion of the matrix. Matrices or compositions formed from hydrophobic α(1→4)glucopyranose polymers with linker portions that include a silyl ether group can exhibit faster degradation rates, allowing for the degradation in a shorter period of implantation. The enhanced degradation is thought to be caused by increased susceptibility of the linker segments containing silyl ether groups to non-enzymatic hydrolytic attack. Non-enzymatic hydrolysis cleaves the covalent bond between the oxygen and silicon atoms in the silyl ether group, and causes loss of the one or more hydrocarbon group(s). This, in turn, reduces hydrophobicity of the matrix or composition and further promotes non-enzymatic hydrolysis. Loss of the hydrocarbon groups also increases susceptibility of the α(1→4)glucopyranose portion to enzymatic degradation by amylases. Degradation of the matrix can result in the release of, for example, naturally occurring mono- or disaccharides, such as glucose, which are common serum components.

In some aspects, a polymeric matrix or composition formed from the hydrophobic α(1→4)glucopyranose polymer with a linker segment that includes a silyl ether group is associated with an implantable or injectable medical article that is capable of releasing a bioactive agent in a subject. The hydrophobic α(1→4)glucopyranose polymer can be used in association with the device to modulate or facilitate preparation of an article that includes and is capable of releasing the bioactive agent. For example, in some aspects bioactive agent can be present within the matrix or composition formed from the hydrophobic α(1→4)glucopyranose polymer. Bioactive agent can be released from the matrix or composition by elution, degradation of the polymer, or both. Since the matrix or composition can be completely degraded in the body, the total amount of the bioactive agent contained in the matrix can be made available to the subject after the matrix degrades. This allows the implantable or injectable medical article to be particularly useful for the treatment of medical conditions that require delivery of therapeutically effective amounts of a bioactive agent over a defined period of treatment.

In other aspects, the polymeric matrix formed from the hydrophobic α(1→4)glucopyranose polymer is in a form that is capable of modulating the releasing a bioactive agent. For example, the matrix can be in the form of a bioactive agent release barrier on an implantable article, such as a polymeric top coat, or an encapsulating shell around a microparticle. Prior to degradation of the release barrier, release of the bioactive agent is restricted, or largely prevented. Following implantation or injection, the barrier layer is capable or degrading in a shorter, defined period of time, after which the bioactive agent can be released.

In yet other aspects, the polymeric matrix is formed into an implantable medical article having a structure or configuration that is useful for treating a medical condition at the site of implantation. For example, the implantable medical article has a structure that provides a prosthetic function at a site of implantation, such as an intraluminal prosthesis. The article provides a structural function at the site of implantation for a period of time, which treats the medical condition, and then degrades.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The invention is generally directed to hydrophobic α(1→4)glucopyranose polymers with pendent groups linked to the α(1→4)glucopyranose backbone. The pendent groups include (a) a linker segment that includes a silyl ether group, and (b) one or more hydrocarbon groups. The invention is also directed to compositions that include these polymers and articles that are formed from or associated with these polymers. The invention is also directed to uses of articles formed from these polymers, such as localized drug delivery.

Generally, the hydrophobic α(1→4)glucopyranose polymer has at least two main portions. The first portion is an α(1→4) glucopyranose polymeric backbone. The second portion is a group, or generally a plurality of groups, pendent from the α(1→4)glucopyranose polymeric backbone (also referred to herein as "pendent groups").

The hydrophobic α(1→4)glucopyranose polymer includes a pendent group, and generally a plurality of pendent groups, that comprises at least one hydrocarbon group. The hydrocarbon groups, collectively, provide sufficient hydrophobicity to the hydrophobic α(1→4)glucopyranose polymer. Therefore, the hydrocarbon groups, taken together, constitute the hydrophobic portion of the polymer. In many aspects, a hydrocarbon group will be positioned at the terminus of a pendent group (i.e., distal from the α(1→4)glucopyranose polymer backbone).

The pendent groups can also include a linker segment between the one or more hydrocarbon group(s) and the glucopyranose monomeric unit to which the pendent group is attached. In all or a portion of the pendent groups, the linker segment includes a silyl ether group. For convenience of discussion, these silyl ether-containing hydrophobic α(1→4) glucopyranose polymer are referred to herein as "hydrophobic α(1→4)glucopyranose polymers." In some cases, the hydrophobic α(1→4)glucopyranose polymer includes pendent groups having a linker segment chemistry that is different than a silyl ether group.

Overall, the hydrophobic α(1→4)glucopyranose polymer displays hydrophobic properties. The polymer can be used to form a hydrophobic α(1→4)glucopyranose matrix or a non solidified polymer-containing mass. For example, the hydrophobic matrix can be in the form of a degradable coating or an implantable drug delivery device. As another example, the article is in the form of an in situ-formed polymeric droplet.

The one or more hydrocarbon group(s) in the pendent group can include saturated hydrocarbon group(s) or unsaturated hydrocarbon group(s). The pendent group may also include a combination of saturated and unsaturated hydrocarbon groups. Examples of hydrocarbon groups include linear and branched alkyl, alkenyl, alkynyl, as well as cyclic alkyl, cyclic alkenyl, aromatic hydrocarbon, and aralkyl groups In some aspects, the pendent group includes a hydrocarbon group that is a monovalent hydrocarbon radical, such as a group of covalently bonded carbon atoms having the formula —$(CH_n)_m$—$CH_3$, wherein m is 0, 1, or greater than 1, and n is independently 2 or 1. A monovalent hydrocarbon radical can be positioned at the terminus of the pendent group and covalently bonded to the silicon atom (i.e., distal from the polysaccharide backbone).

Optionally, the pendent group includes a hydrocarbon group that is a divalent hydrocarbon radical, such as a group of covalently bonded carbon atoms having the formula —$(CH_n)_m$—, wherein m is 1 or greater, and n is independently 2 or 1. If the pendent group includes a hydrocarbon group that is a divalent hydrocarbon radical, it can be separated from another hydrocarbon group by a carbon of a non-hydrocarbon group, or a non-carbon organic heteroatom.

In some aspects, the hydrocarbon group comprises a linear, branched, or cyclic group containing two or more carbon atoms. In some aspects, the hydrocarbon group is a $C_2$-$C_{18}$-containing, a $C_2$-$C_{10}$-containing, or a $C_4$-$C_8$-containing, linear, branched, or cyclic hydrocarbon group.

An $\alpha(1\rightarrow4)$glucopyranose polymer, which forms the poly-$\alpha(1\rightarrow4)$glucopyranose portion of the hydrophobic $\alpha(1\rightarrow4)$ glucopyranose polymer, includes repeating $\alpha$-D-glucopyranose ($Glc_p$) monomers having $\alpha(1\rightarrow4)$ linkages. A portion (three monomeric units) of an $\alpha(1\rightarrow4)$ glucopyranose polymer (shown without the pendent group containing the hydrocarbon and silyl ether groups) is shown below:

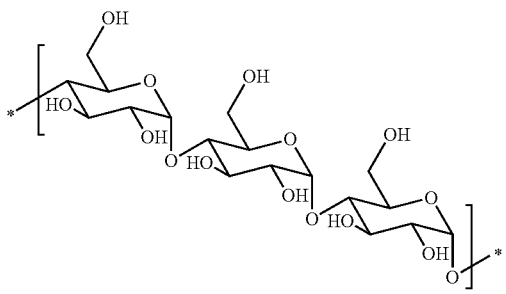

As starting material for the preparation of the silyl ether-containing hydrophobic $\alpha(1\rightarrow4)$glucopyranose polymer, one can use exemplary $\alpha(1\rightarrow4)$glucopyranose polymers, such as maltodextrin, amylose, cyclodextrin, and polyalditol (polyalditol is available from GPC (Muscatine, Iowa) under the tradename Innovatol™ PD60, and has <1% reducing sugars). Maltodextrins generally refer to those polymer preparations having a lower molecular weight than amylose preparations. Cyclodextrins are low molecular weight cyclic $\alpha(1\rightarrow4)$glucopyranose polymers.

Maltodextrin is typically generated by hydrolyzing a starch slurry with a heat-stable $\alpha$-amylase at temperatures at 85-90° C. until the desired degree of hydrolysis is reached and then inactivating the $\alpha$-amylase by a second heat treatment. The maltodextrin can be purified by filtration and then spray dried to a final product. Maltodextrins are typically characterized by their dextrose equivalent (DE) value, which is related to the degree of hydrolysis defined as: DE=MW dextrose/number-averaged MW starch hydrolysate×100. Generally, maltodextrins are considered to have molecular weights that are less than amylose molecules.

A starch preparation that has been totally hydrolyzed to dextrose (glucose) has a DE of 100, whereas starch has a DE of about zero. A DE of greater than 0 but less than 100 characterizes the mean-average molecular weight of a starch hydrolysate, and maltodextrins are considered to have a DE of less than 20. Maltodextrins of various molecular weights are commercially available.

As used herein, "amylase" or "amylose polymer" refers to a linear polymer having repeating glucopyranose units that are joined by $\alpha$-1,4 linkages. Some amylose polymers can have a very small amount of branching via $\alpha$-1,6 linkages (about less than 0.5% of the linkages) but still demonstrate the same physical properties as linear (unbranched) amylose polymers do. Generally amylose polymers derived from plant sources have molecular weights of about $1\times10^6$ Da or less. Amylopectin, comparatively, is a branched polymer having repeating glucopyranose units that are joined by $\alpha$-1,4 linkages to form linear portions and the linear portions are linked together via $\alpha$-1,6 linkages. The branch point linkages are generally greater than 1% of the total linkages and typically 4%-5% of the total linkages. Generally amylopectin derived from plant sources have molecular weights of $1\times10^7$ Da or greater.

Exemplary maltodextrin and amylose polymers have molecular weights ranging from about 500 Da to about 500,000 Da, about 1000 Da to about 300,000 Da, and about 5000 Da to about 100,000 Da.

Maltodextrin and amylose polymers of various molecular weights are commercially available from a number of different sources. For example, Glucidex™ 6 (ave. molecular weight ~95,000 Da) and Glucidex™ 2 (ave. molecular weight ~300,000 Da) are available from Roquette (France); and MALTRIN™ maltodextrins of various molecular weights, including molecular weights from about 12,000 Da to 15,000 Da are available from GPC (Muscatine, Iowa).

In a preferred aspect, the hydrophobic $\alpha(1\rightarrow4)$glucopyranose polymer is formed from a low molecular weight linear polymers such as maltodextrin or amylose. The decision of using maltodextrin or amylose of a particular size range may depend on factors such as the physical characteristics of the composition, the desired rate of degradation of the matrix formed from the polysaccharide, and the presence of other optional components in the matrix, such as bioactive agents.

Refinement of the molecular weight of a polymer preparation (such as the $\alpha(1\rightarrow4)$glucopyranose polymer starting material) can be carried out using diafiltration. Diafiltration of polysaccharides such as maltodextrin can be carried out using ultrafiltration membranes with different pore sizes. As an example, use of one or more cassettes with molecular weight cut-off membranes in the range of about 1K to about 500 K can be used in a diafiltration process to provide polysaccharide preparations with average molecular weights in the range of less than 500 kDa, in the range of about 100 kDa to about 500 kDa, in the range of about 5 kDa to about 30 kDa, in the range of about 30 kDa to about 100 kDa, in the range of about 10 kDa to about 30 kDa, or in the range of about 1 kDa to about 10 kDa.

The polymers as discussed herein can be described in terms of molecular weight. "Molecular weight," as used herein, more specifically refers to the "weight average molecular weight" or $M_w$, which is an absolute method of measuring molecular weight and is particularly useful for measuring the molecular weight of a polymer (preparation). Polymer preparations typically include polymers that individually have minor variations in molecular weight. In some cases, the polymers have a relatively higher molecular weight (e.g., versus smaller organic compounds) and such minor variations within the polymer preparation do not affect the overall properties of the polymer preparation (for example, the characteristics of an polymer preparation). The weight average molecular weight ($M_w$) can be defined by the following formula:

$$M_w = \frac{\sum_i N_i M_i^2}{\sum_i N_i M_i}$$

wherein N represents the number of moles of a polymer in the sample with a mass of M, and $\Sigma_i$ is the sum of all $N_i M_i$ (species) in a preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W., *Contemporary Polymer Chemistry*; pg 271 (1990).

In forming the hydrophobic α(1→4)glucopyranose polymer, and in some modes of practice, a compound having hydrocarbon and silyl ether groups is covalently coupled a portion of an α(1→4)glucopyranose polymer. Typically, the compound is reacted with the natural hydroxyl groups of an α(1→4)glucopyranose polymer to provide a plurality of pendent groups, the pendent groups present at a desired level of substitution on the α(1→4)glucopyranose polymer.

In underivatized or partially derivatized form, the glucopyranose units of an α(1→4)glucopyranose polymer includes monomeric units having glucopyranose ring structures with primary and secondary hydroxyl groups. Primary and/or secondary hydroxyl groups can be reacted with a hydroxyl-reactive compound to provide a pendent group that replaces the primary and/or secondary hydroxyl group on the glucopyranose monomeric unit. The formed pendent group includes one or more hydrocarbon group(s) (which provides at least a portion of the hydrophobic part of the modified polysaccharide), and one or more hydrocarbon group(s) is/are linked to the glucopyranose monomeric unit via a linker segment including a silyl ether group.

In many cases, the silyl ether group replaces one or more original hydroxyl group(s) on the glucopyranose monomeric unit. Pendent groups can be formed on positions on the glucopyranose monomeric units previously corresponding to either or both primary and/or secondary hydroxyl group locations. In many preparations more of the primary hydroxyl groups than secondary hydroxyl groups become derivatized with the pendent groups containing the one or more hydrocarbon group(s) and the silyl ether group.

As stated, the hydrophobic α(1→4)glucopyranose polymer can be formed by reacting a compound that includes a hydrocarbon group and a reactive silicon group, with a hydroxyl group on the glucopyranose monomeric unit. The compound can include a hydroxyl-reactive, silyl ether-forming group.

In one mode of practice, pendent groups are formed by reacting a α(1→4)glucopyranose polymer with a silane compound having the Formula I:

$R^1 R^2 R^3 SiX$ or a silazane compound of Formula II $R^1 R^2 R^3 SiNHSiR^3 R^2 R^1$ wherein in Formula II, $NHSiR^3 R^2 R^1$ is a leaving group. In either Formula I or Formula II, one or more of $R^1$, $R^2$, and/or $R^3$ are independently selected from and include a $C_1$-$C_{18}$ hydrocarbon group, with the proviso that the total number of carbon atoms in $R^1$, $R^2$, and/or $R^3$ is at least three. In Formula I X is a leaving group (e.g., halogen atom, triflate, or cyanide). In either Formula I or Formula II, if $R^1$, $R^2$, or $R^3$ is not a $C_1$-$C_{18}$ hydrocarbon group then $R^1$, $R^2$, or $R^3$ can be H. Preferably X is Cl or H.

Exemplary compounds of Formula I include halogenated alkyl silanes.

In some modes of practice, the total number of carbon atoms in $R^1$, $R^2$, and/or $R^3$ is in the range of 3-12, such as in the range of 4-8, or in the range of 6-12. In some modes of practice, one or more of $R^1$, $R^2$, and/or $R^3$ are independently selected from selected from methyl and ethyl. In some modes of practice, two or more of $R^1$, $R^2$, and/or $R^3$ are independently selected from selected from methyl and ethyl. In some modes of practice, one of $R^1$, $R^2$, and/or $R^3$ is a $C_3$-$C_{10}$ hydrocarbon group, $C_3$-$C_8$ hydrocarbon, or $C_4$-$C_{10}$ hydrocarbon group. In some modes of practice, one of $R^1$, $R^2$, and/or $R^3$ is an isopropyl or tert-butyl group. In some modes of practice, two of $R^1$, $R^2$, and $R^3$ are methyl, and one of $R^1$, $R^2$, or $R^3$ is a $C_4$-$C_{10}$ hydrocarbon group.

Various halogenated alkyl silanes can be reacted with the α(1→4)glucopyranose polymer to form pendent groups containing hydrocarbon and a silyl ether groups. Examples of halogenated alkyl silanes include, but are not limited to, chlorotrimethylsilane, benzylchlorodimethylsilane, bromotriethylsilane, bromotrimethylsilane, butyl(chloro)dimethylsilane, chloro(dimethyl)isopropylsilane, chloro(dimethyl)octylsilane, chloro(dimethyl)phenylsilane, chloro(dimethyl)thexylsilane, chloro(dodecyl)dimethylsilane, chloro(methyl)diphenylsilane, chloro(methyl)phenylsilane, chloro-decyl-dimethylsilane, chloro-isopropyl-dimethylsilane, chlorocyclohexyldimethylsilane, chlorodiethylisopropylsilane, chlorodiisopropyloctylsilane, chlorodiisopropylsilane, chlorodimethylethylsilane, chlorodimethylsilane, chlorophenylsilane, chlorotributylsilane, chlorotriethylsilane, chlorotrihexylsilane, chlorotriisobutylsilane, chlorotriisopropylsilane, chlorotrimethylsilane, chlorotripropylsilane, and the like. Halogenated alkyl silanes are commercially available from Sigma Aldrich Compounds, such as halogenated alkyl silanes, provide pendent groups containing hydrocarbon and silyl ether groups when reacted with hydroxyl groups of the monomeric units along the length of the α(1→4)glucopyranose polymer. The hydrophobic α(1→4)glucopyranose polymer can also include underivatized glucopyranose monomeric units. In other words, methods of synthesis can yield hydrophobic α(1→4)glucopyranose polymers that include monomeric units that remain in their natural state, and that do not react with the alkyl silane compound.

Optionally, the hydrophobic poly(α(1→4)glucopyranose can be synthesized having a combination of pendent groups with different hydrocarbon chemistries. For example, a particular hydrophobic poly(α(1→4)glucopyranose can include pendent groups with two or more different hydrocarbon groups, respectively. For example, the hydrophobic polysaccharide can be synthesized using a mixture of different halogenated alkyl silanes which provide pendent groups with different alkyl chemistries. Optionally, the hydrophobic poly (α(1→4)glucopyranose have pendent groups with different hydrocarbon chemistries as well as linker chemistries that include a silyl ether group as well as one or more other non-silyl ether groups, such as an ester, carbonate, or thioester linkage.

The amount of groups pendent from the polymer backbone can be described by a degree of substitution (DS), which is defined as the average number of pendent groups linked to each sugar residue. Since each sugar residue in an α(1→4) glucopyranose polymer has three hydroxyls available for modification, DS values range from zero to three (full substitution). For example, the hydrophobic α(1→4)glucopyranose polymer can have pendent groups containing the hydrocarbon and silyl ether group at a degree of substitution in the range of 0.2 to 3.0.

The type of hydrocarbon group or groups present in the hydrophobic α(1→4)glucopyranose polymer can also influence the hydrophobic properties of the polymer. Generally, if compounds having large hydrocarbon groups (e.g., longer alkyl groups) are used for the synthesis of the hydrophobic α(1→4)glucopyranose polymer, a smaller amount of the compound may be needed for reaction with the poly(α(1→4) glucopyranose to provide hydrophobicity. In other words, as the chain length, or branching, of the alkyl group increases, the amount of the compound needed to provide a hydrophobic polysaccharide can decrease. Shorter hydrocarbon groups typically are substituted at a higher DS, whereas longer hydrocarbon group are typically substituted at a lower DS.

For example, if a compound (e.g., a halogenated alkyl silane) having a hydrocarbon group with an alkyl chain length of $C_x$ is used to prepare a hydrophobic polysaccharide with a DS of 1, a compound having a hydrocarbon group with an alkyl chain length of $C_{(2x)}$ is reacted in an amount to provide a hydrophobic polysaccharide (with comparable hydrophobicity) with a DS of 0.5.

The degree of substitution can influence the hydrophobic character of the polysaccharide. In turn, polymeric matrices or compositions formed from silyl ether-containing hydrophobic α(1→4)glucopyranose polymers having a high weight ratio of the hydrophobic portion to the α(1→4)glucopyranose polymer (as exemplified by a high DS) are generally more hydrophobic and can be more resistant to degradation. For example, a matrix formed from maltodextrin-silyl ether DS 1.0 may have a rate of degradation that is faster than a matrix formed from maltodextrin-silyl ether DS 1.5.

The size of the hydrocarbon group in the pendent groups can also affect the property of the hydrophobic α(1→4)glucopyranose polymer. Increasing the size of the hydrocarbon group, for example, using one with a longer alkyl chain, such as greater than 8 carbon atoms, wherein the total number of carbon atoms in the pendent group is 10 or greater, can cause the polymer preparation to have an oily consistency. With a lower number of carbon atoms (e.g., less than 10) polymer preparation may take on a solid form. A high degree of substitution with the pendent groups (about 2.5 DS or greater) can also provide a polymer preparation with an oily consistency In preparing the hydrophobic α(1→4)glucopyranose polymer any suitable synthesis procedure can be performed. Synthesis can be carried out to provide a desired number of pendent groups containing hydrocarbon and silyl ether groups from the polysaccharide backbone. The number and/or density of the pendent groups can be controlled, for example, by controlling the relative concentration of one or more compounds (e.g., a halogenated alkyl silane) that provides the pendent groups, to the available reactive groups (e.g., hydroxyl groups) on the polysaccharide.

The following general process outline steps describing reagent types and use of reagents in suggested ranges to provide a hydrophobic α(1→4)glucopyranose with pendent silyl ether-containing groups. In order to provide a desired product, one of skill could modify the process by substituting the cited reagents with similar reagents, in amounts appropriate to provide a hydrophobic polysaccharide.

In one mode of practice, the silyl ether-containing hydrophobic α(1→4)glucopyranose polymer is formed by first using a general base catalyst to activate the hydroxyl group on the polysaccharide, forming an alkoxide ion. Next an alkyl chlorosilane compound is mixed with the activated polysaccharide, causing nucleophilic attack of the alkoxide ion on the alkyl chlorosilane to form a covalent ether linkage between the polysaccharide backbone and the silicon atom of the newly formed pendent group.

Preparation of a hydrophobic α(1→4)glucopyranose polymer can be carried out using a process as follows. In dry form, a molar excess of maltodextrin having a starting molecular weight in the range of about 1-500 kDa is combined with a general base catalyst. An exemplary general base catalyst is imidazole, which can be used in about 0.2-3 times the molar amount of maltodextrin. The components can then be dissolved in a polar aprotic solvent, such as DMSO, to provide a concentration of maltodextrin of approximately 100 mg/mL.

Next, a selected halogenated alkyl silane (or mixture of halogenated alkyl silanes) is added to the activated maltodextrin mixture in an amount to provide a desired level of polysaccharide derivation. As an example, chlorotriethylsilane is added to the activated maltodextrin mixture in an amount of approximately 1.23-21.6 mmol (of chlorotriethylsilane) per gram of maltodextrin. The activated maltodextrin can then be reacted with the chlorotriethylsilane at about room temperature for a period of time of greater than 2 hours. Optionally, derivation can be performed with one or more additional components that provide pendent hydrocarbon-containing groups, such as fatty acid anhydrides or alkyl succinates.

Purification of the reaction product can be performed by the addition of water to the reaction solution, which causes precipitation of the silyl ether-containing hydrophobic α(1→4)glucopyranose polymer. The precipitated polymer can then be dried under vacuum to obtain a solid product, which may exhibit waxy characteristics.

In another mode of practice, the hydrophobic α(1→4) glucopyranose polymer is formed by steps including first reacting an α(1→4)glucopyranose polymer with a compound to provide first pendent hydrophobic groups which include a non-silyl ether linker segment, then reacting with a compound to provide second pendent groups which include a silyl ether linker segment. In this approach, the first step provides a modified α(1→4)glucopyranose polymer (i.e., an intermediate polymer product) that has enhanced solubility in a solvent, such as methylene chloride, used for the subsequent silyl ether modification. The enhanced solubility properties can allow for improved reaction between the silyl ether-forming (e.g., chloroalkyl silane) compound and the intermediate polymer product, and better overall control of pendent group loading. In this embodiment, the second (silyl ether linker) pendent groups have a DS that is greater than the first pendent groups.

For example, in a first step an α(1→4)glucopyranose polymer is reacted with a fatty acid or derivative thereof, such as a fatty acid anhydride or fatty acid halide. Exemplary fatty acids and anhydrides include acetic, propionic, butyric, isobutyric, valeric (pentanoic), caproic (hexanoic), caprylic (octanoic), capric (decanoic), and lauric (dodecanoic) acids and anhydrides, respectively. Reaction of the hydroxyl group can form a pendent group with an ester-containing linker segment (a non-silyl ether linker segment) between the hydrocarbon group the monomeric unit of the α(1→4)glucopyranose polymer.

Reaction can be carried out to provide pendent hydrophobic groups with the non-silyl ether linker segment, at a DS of about 0.5 or less, such as in the range of about 0.1 DS to 0.5 DS, and more preferably in the range of 0.2 DS to about 0.4 DS. In one exemplary mode of synthesis maltodextrin (100-500 kDa) is dissolved in dimethylsulfoxide (DMSO) at about 200 mg/mL in the presence of methylimidazole at about 10 mmol/gram. Hexanoic anhydride is then added at a mole to weight ratio (hexanoic anhydride/maltodextrin) about 2.6 mmol/gram. The reaction takes place at room temperature for a period of time, and then is quenched with water. The modified maltodextrin (MD-hexanoate) can then be collected by vacuum filtration, washed with water, and further purified by dialysis. The MD-hexanoate can then be dissolved in a solvent such as methylene chloride and reacted with a silane containing compound as described herein (e.g., see formulas I and II).

The subsequent reaction with the silane compound can be carried out in a solvent such as methylene chloride, and using a chloroalkyl silane compound such as chlorotriethylsilane and a base catalyst such as imidazole as described herein. The amount of chloroalkyl silane compound used provides a total DS of up to about 2.5, such as in the range of about 1.5 DS to about 2.5 DS, and more preferably about 1.5 DS to about 2.5 DS. Therefore exemplary loads of the first (non-silyl ether linker) pendent group is in the range of about 0.1 DS to 0.5 DS, and the second (silyl ether linker) pendent group is in the range of about 1.0 DS to about 2.4 DS, about 1.3 DS to about 2.1 DS, and preferably about 1.5 DS to about 1.9 DS.

The relationship between portions of the derivatized polymer, for example, the poly-$\alpha(1\rightarrow4)$glucopyranose portion, the hydrophobic portion (the hydrocarbon groups, taken together), and the linker segment containing the silyl ether groups, can be expressed in various ways, such as by weight to weight ratios, by weight to molar amount ratios, and/or by molar amount to molar amount ratios.

For example, the relationship between the hydrophobic portion (i.e., the hydrocarbon groups, taken together) and the poly-$\alpha(1\rightarrow4)$glucopyranose portion can be expressed by the weight ratio between the two. The relationship can be calculated by comparing the amount by weight of the starting $\alpha(1\rightarrow4)$glucopyranose polymer to the amount by total weight of the hydrocarbon groups in the pendent groups (the hydrophobic portion). For purposes of discussion, the hydrophobic portion refers to the sum of the weight of all the hydrocarbon groups that contribute to the hydrophobic property of the polymer.

For example, chlorotriethylsilane has a molecular weight of approximately 150.7 Da (g/mol), and the hydrocarbon portion (the three ethyl groups bonded to the silicon atom) of this molecule constitutes approximately 49.5% by weight of the chlorotriethylsilane (or 87 g/mol). In an exemplary mode of synthesis, maltodextrin is reacted with chlorotriethylsilane at a weight ratio of approximately 1:2, respectively (1 g:2 g). In view of a theoretically complete reaction (i.e., 100% of the chlorotriethylsilane reacts with hydroxyl groups on the maltodextrin) the weight ratio of the $\alpha(1\rightarrow4)$glucopyranose polymer (maltodextrin) to the hydrophobic portion (e.g., in this mode of synthesis, the weight sum of the ethyl groups added to the maltodextrin) is approximately 1:1.2. In some aspects, the hydrophobic portion is derived from the reaction of compound that provides a silyl ether linkage, as well as one or more other compounds that provides a linkage that is different than a silyl ether linkage, such as an ester, carbonate, or thioester linkage.

In some aspects, the poly-$\alpha(1\rightarrow4)$glucopyranose portion and the hydrophobic portion are present at a weight ratio of about 11:1, respectively, (about 8 wt %) or greater, such as in the range of about 11:1 to about 1:10, respectively.

In many aspects, the polysaccharide portion and the hydrophobic portion (i.e., the pendent hydrophobic groups) comprise the predominant portion of the hydrophobic polysaccharide. In other words, on a weight basis, the combined weight of the polysaccharide portion and the hydrophobic portion comprise the majority of the weight of the silyl ether-containing hydrophobic $\alpha(1\rightarrow4)$glucopyranose polymer.

The silyl ether-containing hydrophobic $\alpha(1\rightarrow4)$glucopyranose polymer can include modified and unmodified glucopyranose monomeric units. Generally, the presence of a pendent group on a monomeric unit means that the monomeric unit has been "modified." The pendent group can include one or more hydrocarbon groups that are covalently bonded to the silicon atom, and an oxygen atom linking the silicon atom to the monomeric unit of the $\alpha(1\rightarrow4)$glucopyranose polymer. The silyl ether-containing hydrophobic $\alpha(1\rightarrow4)$glucopyranose polymer can also include unmodified monomeric units. A silyl ether-containing hydrophobic $\alpha(1\rightarrow4)$glucopyranose polymer can also be described by the percentage (or ratio) of modified monomeric units to the unmodified monomeric units. Whether or not a hydrophobic $\alpha(1\rightarrow4)$glucopyranose polymer contains any unmodified monomeric units generally depends on the amount of hydroxyl groups reacted to provide a desired degree of substitution.

A pendent group can be formed from a primary hydroxyl groups on a monomeric unit, from a secondary hydroxyl group on the monomeric unit, or from both primary and secondary hydroxyl groups on a monomeric unit. In many preparations, the silyl ether-containing hydrophobic $\alpha(1\rightarrow4)$ glucopyranose polymer has a plurality of pendent groups wherein more primary hydroxyl groups (versus secondary hydroxyl groups) become derivatized with the pendent groups containing the silyl ether segment and one or more hydrocarbon group(s).

In some aspects the silyl ether-containing hydrophobic $\alpha(1\rightarrow4)$glucopyranose polymer includes a derivatized monomeric unit of Formula III:

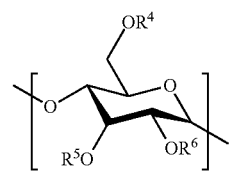

wherein one or more of $R^4$, $R^5$, and/or $R^6$ is according to Formula IV:

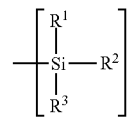

wherein one or more of $R^1$, $R^2$, and/or $R^3$ are independently selected from and include $C_1$-$C_{18}$ hydrocarbon groups, with the proviso that the total number of carbon atoms in $R^1$, $R^2$, and/or $R^3$ is at least three. In sub-Formula IIIa, all of $R^4$, $R^5$, and $R^6$ are according to Formula IV; in sub-Formula IIIb, $R^4$ and one of $R^5$ or $R^6$ are according to Formula IV, where $R^5$ or $R^6$ that are not Formula IV are —H; in sub-Formula IIIc, $R^4$ is according to Formula IV, and $R^5$ and $R^6$ are H.

The $C_1$-$C_{18}$ hydrocarbon group of one or more of $R^1$, $R^2$, and/or $R^3$ can be a linear, branched, or cyclic hydrocarbon structure. Combinations of linear, branched, or cyclic hydrocarbon structures can also be present in the pendent group. In some aspects, one or more of $R^1$, $R^2$, and/or $R^3$ is a linear $C_2$-$C_{18}$ hydrocarbon group. In some aspects, one or more of $R^1$, $R^2$, and/or $R^3$ is a branched $C_2$-$C_{18}$ hydrocarbon group. In some aspects, one or more of $R^1$, $R^2$, and/or $R^3$ is a $C_4$-$C_{12}$ hydrocarbon group. In some aspects, one or more of $R^1$, $R^2$, and/or $R^3$ is a $C_4$-$C_8$ hydrocarbon group.

In some modes of practice, the total number of carbon atoms in $R^1$, $R^2$, and/or $R^3$ is in the range of 3-12, or more preferably in the range of 4-8, or in the range of 6-12. In some modes of practice, one or more of $R^1$, $R^2$, and/or $R^3$ are independently selected from selected from methyl and ethyl. In some modes of practice, two or more of $R^1$, $R^2$, and/or $R^3$ are independently selected from selected from methyl and ethyl. In some modes of practice, one of $R^1$, $R^2$, and/or $R^3$ is a $C_3$-$C_8$ hydrocarbon group, $C_3$-$C_8$ hydrocarbon, or $C_4$-$C_{10}$ hydrocarbon group. In some modes of practice, one of $R^1$, $R^2$, and/or $R^3$ is an isopropyl or tert-butyl group. In some modes of practice, two of $R^1$, $R^2$, and $R^3$ are methyl, and one of $R^1$, $R^2$, or $R^3$ is a $C_4$-$C_{10}$ hydrocarbon group.

In some aspects, the derivatized monomeric unit of Formula III has one or more of $R^4$, $R^5$, and/or $R^6$ according to Formula IV, and the one or more of $R^4$, $R^5$, and/or $R^6$ that are not according to Formula IV are:

—$R^7R^8$ wherein $R^7$ is selected from —C(O)—, —C(O)O—, and —C(O)S—, and $R^8$ is a $C_1$-$C_{18}$ hydrocarbon group. For example, the $C_1$-$C_{18}$ hydrocarbon group ($R^8$) can be linked to the polysaccharide via an ester, carbonate, or thioester linkage. $R^8$ can be a $C_1$-$C_{18}$ hydrocarbon group selected from linear and branched alkyl, alkenyl, alkynyl, cyclic alkyl, cyclic alkenyl, aromatic hydrocarbon, and aralkyl groups. Preferably, $R^8$ is a linear $C_4$-$C_{12}$ hydrocarbon group, such as a linear $C_6$ group. For $R^4$, $R^5$, and/or $R^6$ that are not either Formula IV or —$R^7R^8$, $R^4$, $R^5$, or $R^6$ is H.

In sub-Formula IIId, $R^4$ is —$R^7R^8$, and one or $R^5$ or $R^6$ is according to Formula IV, where $R^5$ or $R^6$ that are not according to Formula IV are —H; in sub-Formula IIIe, $R^4$ is —$R^7R^8$, and both $R^5$ and $R^6$ are according to Formula IV.

In some aspects, the hydrophobic α(1→4)glucopyranose polymer includes one of the following combinations: (a) monomers according to sub-Formulas IIIb and IIId; (b) monomers according to sub-Formulas IIIc and IIId; or (c) monomers according to sub-Formulas IIIa and IIId. In any one of arrangements (a)-(c), the molar quantity of the monomer of sub-Formula IIId is less than the molar quantity of the monomer of sub-Formula IIIb, IIIc, or IIIa, respectively. For example the molar ratio between sub-Formula IIId and sub-Formula IIIb, IIIc, or IIIa in (a)-(c) is in the range of about 1:2 to about 1:10, respectively, such as about 1:4.

In some aspects the hydrophobic α(1→4)glucopyranose polymer includes a derivatized monomeric unit of Formula III and a derivatized monomeric unit of Formula V:

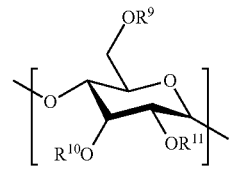

wherein one or more of $R^9$, $R^{10}$, and/or $R^{11}$ are —$R^7R^8$ as defined herein. For $R^9$, $R^{10}$, and/or $R^{11}$ that are not —$R^7R^8$, $R^9$, $R^{10}$, and/or $R^{11}$ is H. In subformula Va, $R^9$ is —$R^7R^8$, and $R^{10}$ and $R^{11}$ are H. In subformula Vb, $R^9$ is —$R^7R^8$, and one or both of $R^{10}$ and $R^{11}$ are —$R^7R^8$.

In some aspects, the hydrophobic α(1→4)glucopyranose polymer includes one of the following combinations: (d) monomers according to sub-Formulas Va and IIIb; (e) monomers according to sub-Formulas Va and IIIc. In arrangements (d) or (e), the molar quantity of the monomer of sub-Formula Va is less than the molar quantity of the monomer of sub-Formula IIIb or IIIc, respectively.

The hydrophobic α(1→4)glucopyranose polymer has the properties of being soluble in halogenated organic solvents such as methylene chloride and chloroform. The solubility of the hydrophobic α(1→4)glucopyranose polymer in a solvent will depend on factors such as the level of derivation with the hydrophobic groups, as well as the particular solvent or combination of solvents used.

Within a particular solvent, the hydrophobic α(1→4)glucopyranose polymer may be determined to be soluble (having a solubility of at least 1 part agent per from 10 to 30 parts solvent), freely soluble (having a solubility of at least 1 part agent per from 1 to 10 parts solvent), or very soluble (having a solubility of greater than 1 part agent per 1 part solvent). These descriptive terms for solubility are standard terms used in the art (see, for example, *Remington: The Science and Practice of Pharmacy*, 20th ed. (2000), Lippincott Williams & Wilkins, Baltimore Md.). The hydrophobic α(1→4)glucopyranose polymer has the properties of being insoluble in water. The term for insolubility is a standard term used in the art, and meaning 1 part solute per 10,000 parts or greater.

In some aspects, a hydrophobic α(1→4)glucopyranose polymer having a molecular weight within a predetermined size range is used. The molecular weight of hydrophobic α(1→4)glucopyranose polymer can be described in terms of the starting molecular weight of the α(1→4)glucopyranose polymer, or the molecular weight of the fully derivatized polymer (i.e., including the pendent groups).

The addition of pendent groups including the hydrocarbon group(s) and silyl ether group will generally cause a measurable increase in molecular weight of the poly α(1→4)glucopyranose polymer from its underivatized, starting molecular weight. The amount increase in molecular weight can depend on one or more factors, the level of derivatization, and the chemical nature of the pendent groups. In one aspect, the hydrophobic α(1→4)glucopyranose polymer has a molecular weight in the range of about 5 kDa to about 5000 kDa, and in more specific aspects a molecular weight in the range of about 25 kDa to about 1000 kDa.

The hydrophobic α(1→4)glucopyranose polymer and compositions including these polymer can optionally be described in terms of glass transition temperatures ($T_g$) and temperature ranges. $T_g$ can be measured by any suitable technique, e.g., dilatometry, refractive index, differential scanning calorimetry, dynamic mechanical measurement, and dielectric measurement. An increase in the size of one or more of $R^1$-$R^3$ groups in the Formula I generally lowers the Tg of the hydrophobic polysaccharide.

If the matrix or composition includes a bioactive agent, release rate of the bioactive agent can be affected by the Tg of the hydrophobic α(1→4)glucopyranose polymer. For example, an increase in the size of the hydrocarbon group can lowers the Tg of the hydrophobic α(1→4)glucopyranose polymer and may increase the release rate of bioactive agent. Conversely, a decrease in the size of the hydrocarbon group can increases the Tg of the hydrophobic α(1→4)glucopyranose polymer and may decrease the release rate of the bioactive agent.

The hydrophobic α(1→4)glucopyranose polymer can be present in a liquid composition including a solvent suitable to dissolve the polymer ("a polymer solvent"). Examples of solvents that can be used to prepare a composition include halogenated alkanes such as methylene chloride and chloroform. Combinations of one or more of these or other solvents can also be used.

The hydrophobic α(1→4)glucopyranose polymer can also be present in a "neat" form, as, for example, an oil, with no solvent present. The polymer can be in substantially neat form, for example, with less than about 10% v/v, or less than about 5% v/v solvent. The hydrophobic α(1→4) glucopyranose polymer in oil form can be viscous. The polymer in neat or substantially neat form can be used as an injectable composition. For example, the injectable composition can include the hydrophobic α(1→4) glucopyranose polymer along with a biocompatible solvent, such as one selected from the group consisting of benzyl benzoate, glycofural, triacetin, and dimethyl isosorbide.

Compositions including dissolved hydrophobic α(1→4) glucopyranose polymer in a solvent, or combination of solvents, can be used for the preparation of coatings, casting films, particulates (such as microparaticles), or the preparation of implantable filaments.

The hydrophobic α(1→4)glucopyranose polymer can also be provided in the form of an emulsion. For example, the hydrophobic α(1→4)glucopyranose polymer can be present in either an oil-in-water-type of emulsion, or a water-in-oil-type of emulsion. An oil-in-water-type of emulsion can include the hydrophobic α(1→4)glucopyranose polymer present in the dispersed phase. An oil-in-water-type of emulsion can be prepared by dissolving the polymer in a polymer solvent such as dichloromethane, chloroform, or another solvent that is immiscible with water. The solvated polymer can be added to an excess amount of continuous phase liquid, such as water or a water-based liquid. The continuous phase liquid can include one or more additional components that can stabilize the emulsion, which in turn can promote the formation of particular discontinuous phase structures. For example, halogenated arylboronic emulsion stabilizers as described in commonly assigned and copending U.S. Application Ser. No. 61/247,408, (Sep. 30, 2009; Slager et al.), such as 3,5-dichlorophenylboronic acid, can be present in the organic phase of the emulsion, either in the continuous phase in a oil-in-water-type of emulation, or the discontinuous phase of the water-in-oil-type of emulsion, in an about in the range of about 0.005 wt % to about 5 wt %.

To form a water-in-oil-type of emulsion, water or a water-based liquid can be dispersed in a continuous phase liquid such as dichloromethane or chloroform having the solubilized hydrophobic α(1→4)glucopyranose polymer. After the discontinuous phase and continuous phase liquids are mixed, the composition can be agitated, such as in a homogenizer, to promote emulsion formation.

The hydrophobic α(1→4)glucopyranose polymer can be used to form articles that are wholly or partially degradable. A partially degradable article can be an article that has a biostable portion, such as a biostable body member, and a biodegradable portion, such as a biodegradable coating. The polymeric matrices formed from the hydrophobic α(1→4) glucopyranose polymers can be used in many medical applications. These include drug delivery medical applications, as well as applications where drug delivery is not required. The applications can involve short term or long-term treatment of various conditions.

In some aspects, the hydrophobic α(1→4)glucopyranose polymer is used to form a body member, or a portion of a body member, of an implantable medical article. In these aspects, a degradable body member, or portion thereof, can provide mechanical properties at the implantation site and can maintain these mechanical properties until they are no longer needed. After a period of time has elapsed, the body member is degraded to an extent that the mechanical properties are no longer provided, and the degraded components of the article are processed by the body.

In some embodiments, the body member of the medical article slowly degrades and transfers stress at the appropriate rate to surrounding tissues as these tissues heal and can accommodate the stress once borne by the body member of the medical article. The medical article can optionally include a coating or a bioactive agent to provide one or more additional functional features; however, these are not required in order for the article to be of use at the treatment site.

The article can also comprise filaments and fibers, such as microfibers and/or nanofibers that are formed from the hydrophobic α(1→4)glucopyranose polymer. The filaments or fibers can be included in or associated with various articles including implantable medical articles. The filaments or fibers may be prepared with a bioactive agent to provide one or more additional functional features.

In another aspect of the invention, the hydrophobic α(1→4)glucopyranose polymer is used to form a coated layer on a surface of a medical article. The hydrophobic α(1→4) glucopyranose polymer can be present in one or more coated layers on all or a portion of the surface of the device. A "coating" as used herein can include one or more "coated layers", each coated layer including one or more coating materials. In some cases, the coating can be formed of a single layer of material that includes the hydrophobic α(1→4)glucopyranose polymer. In other cases, the coating includes more than one coated layer, at least one of the coated layers including the hydrophobic α(1→4)glucopyranose polymer. If more than one layer is present in the coating, the layers can be composed of the same or different materials.

For the formation of a coating, a composition containing the hydrophobic α(1→4)glucopyranose polymer in a solvent system can be applied to the device surface, and then the solvent is removed from the applied composition.

The coating can also include a tie layer that promotes association of the hydrophobic α(1→4)glucopyranose polymer with the device surface. The tie layer can be formed from any biostable or biodegradable polymer. In some aspects, the hydrophobic α(1→4)glucopyranose polymer is used along with a degradable polymeric tie layer material. Exemplary biodegradable tie layer polymers also include α(1→4)glucopyranose polymeric backbones. In some aspects, the tie layer includes reactive chemistries that allow bonding of the polymer to the device surface, and/or the crosslinking of the polymer on the surface. For example, in some aspects the tie layer polymer includes a hydrophobic α(1→4)glucopyranose polymer with a pendent reactive alkoxysilane. These polymers are described in commonly assigned U.S. patent application Ser. No. 12/792,365 entitled "Silane Functionalized Hydrophobic α(1→4)Glucopyranose Polymers and Polymeric Matrices for Implantation or Injection,", filed Jun. 2, 2010 (Kurdyumov et al.).

After the tie layer is formed, a composition including the hydrophobic α(1→4)glucopyranose polymer and a bioactive agent is disposed on the polymeric tie layer, and a polymeric bioactive agent-releasing layer is formed. In the case where a base layer formed from a hydrophobic α(1→4)glucopyranose polymer is used, the hydrophobic α(1→4)glucopyranose polymer may be able to blend into the tie layer to a certain extent, thereby providing a more durable coating where the materials of the drug-releasing layer become partially mixed with the tie layer.

A coating composition (with or without bioactive agent) can be applied to a medical device using standard techniques to cover the entire surface of the device, or a portion of the device surface. If more than one coated layer is applied to a surface, it is typically applied successively. For example, a coated layer can be formed by dipping, spraying, bushing, or swabbing a coating composition including the hydrophobic α(1→4)glucopyranose polymer on the article to form a layer, and then removing the solvent from the applied composition to form the coated layer. The process can be repeated to provide a coating having multiple coated layers, wherein at least one layer includes the hydrophobic α(1→4)glucopyranose polymer. The compositions of the present invention are suitable for use in spray coating processes. An exemplary spray coating process and apparatus that can be used for coating implantable medical articles using the compositions of the present invention is described in U.S. Pat. No. 7,192,484 (Chappa et al.). A composition that includes the hydrophobic α(1→4)glucopyranose polymer can be spray coated directly onto the surface of a body member of a medical article, or can be spray coated onto a surface that includes one or more coated layers of material previously formed on the body member.

The following list of medical articles is provided to illustrate those that can be associated with a polymeric matrix made using the hydrophobic α(1→4)glucopyranose polymer. These types of articles are typically introduced temporarily or permanently into a mammal for the prophylaxis or treatment of a medical condition. For example, these articles can be introduced subcutaneously, percutaneously, or surgically to rest within an organ, tissue, or lumen of an organ, such as arteries, veins, ventricles, or atria of the heart.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septic defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

In some aspects the polymeric matrix made using the hydrophobic α(1→4)glucopyranose polymer is associated with, or made into, an ophthalmic article. For example, the matrix can be used as a coating on the surface of an ophthalmic article, or as a filament or drug delivery depot configured for placement at an external or internal site of the eye. In some aspects, the articles can be utilized to deliver a bioactive agent to an anterior segment of the eye (in front of the lens), and/or a posterior segment of the eye (behind the lens). Illustrative intraocular devices include, but are not limited to, those described in U.S. Pat. No. 6,719,750 B2 (Varner et al.) and U.S. Pat. No. 5,466,233 ("Tack for Intraocular Drug Delivery and Method for Inserting and Removing Same," Weiner et al.) Illustrative ophthalmic devices for subretinal application include, but are not limited to, those described in U.S. Patent Publication No. 2005/0143363 (de Juan et al.).

A polymeric matrix made using the hydrophobic α(1→4) glucopyranose polymer can be associated with a device formed of a non-biodegradable material. For example, a coating can be formed on a body member of a medical article that is partially or entirely fabricated from a plastic polymer. Plastic polymers include those formed of synthetic polymers, including oligomers, homopolymers, and copolymers resulting from either addition or condensation polymerizations. Examples of suitable addition polymers include, but are not limited to, acrylics (e.g, methyl acrylate) and vinyls (e.g., ethylene). Examples of condensation polymers include, but are not limited to, nylons (e.g., polycaprolactam) and also polyurethanes, polycarbonates, polyamides, polysulfones, poly(ethylene terephthalate), polydimethylsiloxanes, and polyetherketones.

The polymeric matrix can also be associated with an implantable medical article partially or entirely fabricated from a degradable polymer. The article can degrade in an aqueous environment, such as by simple hydrolysis, or can be enzymatically degraded. Examples of classes of synthetic polymers that can be used to form the structure of a degradable article include polyesters, polyamides, polyurethanes, polyorthoesters, polycaprolactone (PCL), polyiminocarbonates, aliphatic carbonates, polyphosphazenes, polyanhydrides, and copolymers thereof. As an example, the hydrophobic polysaccharide can provide a barrier coating to articles fabricated from polylactide or copolymers thereof. The coating can shield the article during a portion or all of a desired period of treatment. The coated article can still be fully degradable.

The polymeric matrix can also be associated with an implantable medical article that is partially or entirely fabricated from a metal. Although many devices or articles are constructed from substantially all metal materials, such as alloys, some may be constructed from both non-metal and metal materials, where at least a portion of the surface of the device is metal. Commonly used metals include platinum, gold, or tungsten, as well as other metals such as rhenium, palladium, rhodium, ruthenium, titanium, nickel, and alloys of these metals, such as stainless steel, titaniurn/nickel, nitinol alloys, cobalt chrome alloys, non-ferrous alloys, and platinum/iridium alloys. One exemplary alloy is MP35.

In some aspects a biodegradable coating is formed on the surface of an erodable implantable medical device formed from of a metal. For example, a biodegradable coating can be formed on a magnesium alloy stent that can be corroded following placement in a subject (see, for example, De Mario, C. et al. (2004) *J. Interv. Cardiol.*, 17(6):391-395, and Heublein, B., et al. (2003) *Heart;* 89:651-656). The erodable implantable medical device can be associated with a bioactive agent, if desired.

In aspects where the structure of the implantable medical article is fabricated from a material that is erodable or degradable, an in vivo lifetime of the article can be determined. Using the hydrophobic α(1→4)glucopyranose polymer, a biodegradable coating can be formed the surface of these erodable or degradable articles to prolong their in vivo lifetime. For example, a coating formed from the hydrophobic α(1→4)glucopyranose polymer can provide a hydrophobic biodegradable barrier which protects a degradable body member from degradation for a period of time. Upon degradation of the barrier, the body member can quickly degrade. The in vivo lifetime is a period of time starting upon placement of the coated article at a target location, and ending when the coated article is completely degraded at the target location.

Other medical articles which can be associated with the hydrophobic α(1→4)glucopyranose polymer can be formed from biomaterials such as ceramics including, but not limited to, silicon nitride, silicon carbide, zirconia, and alumina, as well as glass, silica, and sapphire. Combinations of ceramics and metals can also be coated.

The hydrophobic α(1→4)glucopyranose polymer can also be associated with an article having a porous structure, such as one formed of a fabric or that has fabric-like qualities. The porous structure can be formed from textiles, which include woven materials, knitted materials, and braided materials. Particularly useful textile materials are woven materials which can be formed using any suitable weave pattern known in the art. The porous structure can be that of a graft, sheath, cover, patch, sleeve, wrap, casing, and the like, including many of the medical articles described herein. These types of articles can function as the medical article itself or be used in conjunction with another part of a medical article. Other particular contemplated porous structures include grafts, particularly grafts having textured exterior portions. Examples of textured grafts include those that have velour-textured exteriors, with textured or smooth interiors. Grafts constructed from woven textile products are well known in the art and have been described in numerous documents, for example, U.S. Pat. No. 4,047,252; U.S. Pat. No. 5,178,630; U.S. Pat. No. 5,282,848; and U.S. Pat. No. 5,800,514.

A bioactive agent can also be associated with a composition or matrix including the hydrophobic α(1→4)glucopyranose polymer. In some aspects, a bioactive agent-containing coating is provided. The coating can include a coated layer formed using the hydrophobic α(1→4)glucopyranose polymer. In some aspects, one or a combination of bioactive agents can be immobilized in a coated layer formed from the hydrophobic α(1→4)glucopyranose polymer.

The term "bioactive agent," refers to an inorganic or organic molecule, which can be synthetic or natural, that causes a biological effect when administered in vivo to an animal, including but not limited to birds and mammals, including humans. A partial list of bioactive agents is provided below. According to embodiments of the present invention, one may choose one or more of the bioactive agents to be included in an article or coating is associated with a matrix formed from the hydrophobic α(1→4)glucopyranose polymer. A comprehensive listing of bioactive agents, in addition to information of the water solubility of the bioactive agents, can be found in *The Merck Index*, Thirteenth Edition, Merck & Co. (2001).

Articles and coatings prepared according to the invention can be used to release bioactive agents falling within one or more of the following bioactive agent classes. These classes include, but are not limited to: ACE inhibitors, actin inhibitors, analgesics, anesthetics, anti-hypertensives, anti polymerases, antisecretory agents, anti-AIDS substances, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, antiproliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, photodynamic therapy agents, prostaglandins, remodeling inhibitors, statins, steroids, thrombolytic agents, tranquilizers, vasodilators, and vasospasm inhibitors.

In some cases, the hydrophobic groups pendent from the silyl ether-containing α(1→4)glucopyranose backbone have properties of a bioactive agent. In these aspects, the hydrophobic group/bioactive agent can be hydrolyzed from the α(1→4)glucopyranose backbone and released from the matrix to provide a therapeutic effect in a subject. An example of a therapeutically useful compound having a hydrocarbon group is butyric acid, which has been shown to elicit tumor cell differentiation and apoptosis, and is thought to be useful for the treatment of cancer and other blood diseases. Other illustrative compounds comprising hydrocarbon groups include valproic acid and retinoic acid. Retinoic acid is known to possess antiproliferative effects and is thought to be useful for treatment of proliferative vitreoretinopathy (PVR). Another illustrative compound that can be coupled to the polysaccharide backbone is a corticosteroid. An exemplary corticosteroid is triamcinolone.

One method of coupling triamcinolone to a natural biodegradable polymer is by employing a modification of the method described in Cayanis, E. et al., *Generation of an Auto-anti-idiotypic Antibody that Binds to Glucocorticoid Receptor*, The Journal of Biol. Chem., 261(11): 5094-5103 (1986). Triamcinolone succinicate is prepared by reaction of triamcinolone with succinic anhydride; an acid of the resulting triamcinolone succinate is formed and then reacted with the polysaccharide, such as maltodextrin or polyalditol, resulting in pendent triamcinolone groups coupled to the polysaccharide via a linker containing two ester groups.

Thin polymer free standing films can be prepared from a composition including the silyl ether-containing hydrophobic α(1→4)glucopyranose polymer. In some modes of practice, free standing films are prepared by spin casting the polymer on a glass substrate. The formed films can be floated on a water surface, and subsequently handled. The free standing films can be shaped (such as by cutting) to provide a desired configuration.

The hydrophobic α(1→4)glucopyranose polymer can also be used to form a medical implant having a defined structure. In other words, the glucopyranose polymer serves as material (i.e., structural material) for making a body implant. Such an implant can be formed by a process such as molding, extrusion, shaping, cutting, or combinations of these processes. Preferably extrusion is used. Extrusion can be carried out by heating a composition containing the glucopyranose polymer to a temperature greater than its Tg (glass transition temperature), extruding the composition into a desired form, and then cooling. In some modes of practice, the extruded composition is heated to a temperature of about 40° C. or greater, or about 70° C. or greater to cause melting of the polymer. Higher temperatures (such as greater than 100° C.) may be used if a hydrophobic derivative having a higher Tg is used to form the implant. Optionally, a bioactive agent can be included in the extrusion composition. The ingredients can be mixed for a period of time, such as less than 10 minutes, before being extruded. After melting and mixing, the mixture can be extruded out of a die into a desired shape. Further shaping, such as cutting, can be performed after the extruded material cools to provide an implant in a final form.

In other aspects, the hydrophobic α(1→4)glucopyranose polymer is used to form an implantable or injectable medical article which also includes a bioactive agent. The implant may not have any distinct mechanical properties, such as would be apparent with an intravascular prosthesis, but rather provides a mechanism to deliver the bioactive agent to a particular portion of the body. The implant can have a defined structure and size that is appropriate for its use at a desired location in the body. Processes such as extrusion, solvent casting, and emulsion-based techniques, as described herein, can be used to make the implantable or injectable medical article.

In some aspects the an implantable or injectable medical article includes a matrix formed of the hydrophobic α(1→4) glucopyranose polymer which modulates the release of the bioactive agent from the article. In some cases, the matrix is in the form of a barrier layer that the bioactive agent passes through before becoming available to the subject. Such a barrier layer can be in the form of a shell of polymeric material encapsulating a core comprising bioactive agent.

In other aspect, the implant is in the form of a filament, pellet, or the like, which contains a bioactive agent. Such an implant can be formed by a process like solvent casting. A medical implant having a defined structure can be formed by any suitable process, including molding, extruding, shaping, cutting, casting, and the like.

In other aspects, the hydrophobic α(1→4)glucopyranose polymer is used to form a microparticle. Microparticles including a hydrophobic α(1→4)glucopyranose polymer can be formed using an oil-in-water-type emulsion process, a water-in-oil-type emulsion process, or a spray drying process. Microparticles formed using a silyl ether-containing hydrophobic α(1→4)glucopyranose polymer microparticles can include a bioactive agent (such as a large biomolecule bioactive agent, like a protein). Processes such as solid (protein)/oil/water (single emulsion method), or water (aqueous protein solution)/oil/water (double emulsion method) can be used to prepare bioactive agent-containing microparticles.

In one mode of practice, hydrophobic α(1→4)glucopyranose polymer-based microparticles are formed using a water/oil/water (W/O/W) emulsion solvent extraction-evaporation method based on the techniques described in Péan, J.-P. et al. (1999) *Pharma. Res.*, 16:1294-1299. The microparticles formed using this method include a bioactive agent (Péan forms microparticles including nerve growth factor using human serum albumin as a carrier). However, a bioactive agent can be included or omitted from a process based on Péan using hydrophobic α(1→4)glucopyranose, as desired. In some modes of practice, if a bioactive agent is included, it is used in an amount of up to about 10% (with respect to the weight of the hydrophobic α(1→4)glucopyranose polymer).

First, 0.15 mL of an aqueous phase buffered solution (e.g., 16 mM citrate buffer) and 5% human serum albumin (with respect to the amount of hydrophobic α(1→4)glucopyranose used) and containing 10 µg of a polypeptide-based bioactive agent is prepared. This is then added to, and emulsified in an organic solution (e.g., about 1.2-2.0 mL of an organic solvent such as dichloromethane, ethyl acetate, chloroform, etc., or mixtures thereof) containing 500 mg of hydrophobic α(1→4) glucopyranose. Emulsion is performed in a glass vial, suitable volume syringe (capped), or a thermoplastic tube (e.g., PTFE) with a lab mixer (e.g., a Silverson L4RT lab mixer with square hole head or Silverson, Model L4RT, 19 mm Tubular Head or IKA-T25 Ultra-Turrax, S 25 N-G, Coarse 8 mm diameter rotor-stater probe) for about 30-40 seconds. Mixing time can be varied based on the mixing speed and batch size or volume.

For the W/O/W (double emulsion method), after the primary emulsion is formed it is injected into a 100 mL solution of 2% PVA (in water) while homogenizing at 3000 rpm using the above-mentioned mixers for 30-40 sec. This is then poured into 600-700 mL of water, and stirred for 15 min at 300-500 rpm (using a stir-bar), followed by filtration and washing, etc.

For the solid/O/W (single emulsion method), the solid (protein) dispersed polymer solution is injected into a 100 mL solution of 2% PVA (in water) while homogenizing at 3000 rpm using the above-mentioned mixers for 30-40 sec. This is then poured into 600-700 mL of water, and stirred for 15 min at 300-500 rpm (using a stir-bar), followed by filtration and washing, etc.

Bioactive agents incorporated into the microparticles formed using these techniques can release a desired amount of the agent over a predetermined period of time. The bioactive agent can be released from the biodegradable microparticle upon degradation of the biodegradable microparticle in vivo.

In yet another aspect, bioactive agent is present in an injectable composition including the hydrophobic α(1→4)glucopyranose polymer, wherein the composition is capable of forming small droplets (globular masses) of polymeric material that contain bioactive agent. The composition can be in neat form, or substantially neat form, as described herein. The composition can also include a biocompatible solvent, such as one selected from the group consisting of benzyl benzoate, glycofural, triacetin, and dimethyl isosorbide, as described herein. Upon contacting body fluid, the hydrophobic nature of the composition causes its dispersion into small droplets that include and are capable of bioactive agent release. In this sense, the droplets are in situ-formed. In some cases, the bioactive agent in the droplets is in particulate form (e.g., microparticles) and/or is a high molecular weight therapeutic bioactive agent, such as one selected from nucleic acids, for example, siRNA (small interfering RNA), and antisense oligonucleotides, and ribozymes; and peptides, such as monoclonal and polyclonal antibodies, cytokines, growth factors, receptor ligands, and enzymes. High molecular weight therapeutic bioactive agent and/or bioactive agent in particular form can also be present in a polymeric matrix made from the hydrophobic α(1→4)glucopyranose polymer.

Medical articles associated with a matrix formed from the hydrophobic α(1→4)glucopyranose polymer can be treated to sterilize one or more parts of the article, or the entire medical article. Sterilization can take place prior to using the medical article and/or, in some cases, during implantation of the medical article.

In some aspects, the invention provides a method for delivering a bioactive agent from an article associated with a matrix formed from the hydrophobic α(1→4)glucopyranose polymer. The bioactive agent can be present in a matrix formed from the hydrophobic α(1→4)glucopyranose polymer, or associated with a different portion of the article. For example, the matrix formed from the hydrophobic α(1→4) glucopyranose polymer may provide a barrier that the bioactive agent passes through, or the bioactive agent is releasable from a different polymeric layer that is also associated with the article.

In performing the method, the article is placed in a subject. Upon exposure to body fluid the bioactive agent is released from a portion of the article. In some cases, depending on the arrangement of the matrix formed from the hydrophobic α(1→4)glucopyranose polymer in the article is subjected to degradation by non-enzymatic hydrolysis, enzymatic amylase activity, or both. A carbohydrase can promote the degradation of the polymeric matrix. Degradation may occur before, during, or after the release of the bioactive agent. Examples of carbohdrases that can specifically degrade natural biodegradable polysaccharide coatings include α-amylases, such as salivary and pancreatic α-amylases; disaccharidases, such as maltase, lactase and sucrase; trisaccharidases; and glucoamylase (amyloglucosidase).

Serum concentrations for amylase are estimated to be in the range of about 50-100 U per liter, and vitreal concentrations also fall within this range (Varela, R. A., and Bossart, G. D. (2005) *J Am Vet Med Assoc* 226:88-92).

In some aspects, the carbohydrase can be administered to a subject to increase the local concentration, for example in the serum or the tissue surrounding the implanted device, so that the carbohydrase may promote the degradation of the matrix. Exemplary routes for introducing a carbohydrase include local injection, intravenous (IV) routes, and the like. Alternatively, degradation can be promoted by indirectly increasing the concentration of a carbohydrase in the vicinity of the matrix, for example, by a dietary process, or by ingesting or administering a compound that increases the systemic levels of a carbohydrase.

In other cases, the carbohydrase can be provided on a portion of the article. For example the carbohydrase may be eluted from a portion of the article that does not include the matrix. In this aspect, as the carbohydrase is released it locally acts upon the coating to cause its degradation and promote the release of the bioactive agent. The invention will be further described with reference to the following non-limiting Examples.

Example 1

Preparation of Fractionated Maltodextrin

Maltodextrin was purchased from Roquette, France (Glucidex™ 2, MWave 320 kDa) or Grain Processing Corporation, Muscatine, Iowa (M040 MWave 55 kDa). The 55 kDa maltodextrin was used as received. Glucidex™ 2 was further fractionated to a narrower polydispersity. Glucidex™ 2 maltodextrin (MD; 500 g; DE=3 max) was dissolved in deionized water to a total volume of 5 L with stirring, and diafiltered using a 500 kDa molecular weight cut-off cassette, ant the permeate (flow through) was kept. The permeate was then diafiltered using a 100 kDa weight cut-off cassette and the retenate was kept. The solution was concentrated down to 3 L and then lyophilized. 310 g of maltodextrin (100-500 kDa) was isolated (62% yield).

Example 2

Method of Making Maltodextrin-Dimethyldecylsilyl Ether

Maltodextrin (Glucidex 2, 1 g) was placed into 25 mL oven-dried round-bottom flask equipped with the stir bar, under inert atmosphere of nitrogen. DMSO (10 mL) was added and mixture was stirred at room temperature until maltodextrin dissolved. 1-methylimidazole (3 mL, 37.6 mmol) was added at once and solution was allowed to stir for additional 5 min. Chlorodecyldimethylsilane (5 mL, 18.4 mmol) was added dropwise via syringe. Reaction was allowed to stir at room temperature for additional 16 hr. At which point, liquid layer was decanted keeping precipitate inside. Crude product was dissolved in $CH_2Cl_2$ filtered and solvent was evaporated in vacuo. Product was further dried in vacuo resulting in viscous oil.

Example 3

Method of Making Maltodextrin-Dimethylbutylsilyl Ether

Maltodextrin (Glucidex 2, 1 g) was placed into 50 mL oven-dried round-bottom flask equipped with the stir bar, under inert atmosphere of nitrogen. DMSO (10 mL) was added and mixture was stirred at room temperature until maltodextrin dissolved. 1-methylimidazole (1.1 mL, 13.8 mmol) was added at once and solution was allowed to stir for additional 5 min. Chlorobutyldimethylsilane (2.1 mL, 12.2 mmol) was added via syringe dropwise. White gel-like precipitate appeared and floated to the top of the reaction mixture. Reaction was allowed to stir at room temperature for additional 2 hr. At which point, reaction mixture was poured into MeOH (150 mL) and white precipitated formed. Liquid layer was decanted and crude product was washed with MeOH (3×10 mL). Product was further dried in vacuo to obtain solid.

Several maltodextrin-dimethylalkylsilyl ethers were made according to method 4 and 5. They are summarized in Table 1.

TABLE 1

| Polymer | MW maltodextrin | Hydrophobic chain | Theoretical DS |
|---|---|---|---|
| A | 320 kDa | Decyl | 3.0 |
| B | 320 kDa | Butyl | 3.0 |
| C | 320 kDa | Butyl | 2.0 |
| D | 55 kDa | Butyl | 1.5 |
| E | 320 kDa | Decyl | 1.0 |
| F | 320 kDa | Decyl | 2.5 |

Example 4

Degradation of coatings formed from maltodextrin-alkylsilyl ethers polymers was evaluated in PBS, the degradation characterized by mass loss. The maltodextrin-alkylsilyl ethers polymers were used to coat stents, and the degradation of the coating was evaluated.

Bare metal stents (BX Velocity 7 cell×18 mm) were cleaned with chloroform, dried, cleaned a second time with a solution of NaOH in IPA (Enprep), rinsed with water, dried, and weighed.

All stents were coated with a Parylene tie layer prior to coating with maltodextrin-alkylsilyl ethers polymers. To form the Parylene layer, stents were placed in a Parylene coating reactor (PDS 2010 LABCOTER™ 2, Specialty Coating Systems, Indianapolis, Ind.) and coated with Parylene C (Specialty Coating Systems, Indianapolis, Ind.) by following the operating instructions for the LABCOTER™ system.

Polymer C—maltodextrin-butylsilylether 2.0—(Table 1, Example 3) was used for coating compositions to coat the metal stents having the Parylene tie layer.

Maltodextrin-butylsilylether 2.0 was mixed with sirolimus (67 wt % polymer, 33 wt % sirolimus) and dissolved in acetone. The final concentration of the solution was 40 mg/mL total solids. All solutions were filtered (10 μm) before use.

Stents were coated by an ultrasonic spray process and apparatus as described in U.S. Pat. No. 7,192,484 (Chappa et al.). Approximately 600 μg of coating material (Maltodextrin-butylsilylether 2.0/sirolimus) was applied to each stent. Stents were dried under nitrogen to remove residual solvent and weighed.

To assess degradation of the maltodextrin-butylsilylether 2.0 coatings, coated stents (uncrimped, unexpanded) were placed in 1 mL PBS, pH 7.4 and incubated with light shaking at 37° C. At intervals, stents were removed from the solution, rinsed briefly with water to remove salts, blotted dry, and allowed to dry further at ambient conditions or under vacuum for at least 2 h. Samples were then weighed and the weight was compared to initial coating weights to determine the amount of coating lost. After weighing, samples were returned to fresh PBS and the experiment continued. By this method, the mass loss of individual samples was tracked over time. Coating formulations were tested in triplicate.

Coatings of maltodextrin-butylsilylether 2.0 exhibited mass loss when incubated in buffered solutions. The mass loss was faster at acidic or basic conditions than at neutral pH. For example, at day 28, approximately 33% of the coating mass remained at pH 7.0, whereas at day 28, approximately 25% of the coating mass remained at pH 4.0.

What is claimed is:

1. An implantable or injectable medical article, the article comprising a bioactive agent releasable from the article and a biodegradable polymeric matrix or composition comprising a hydrophobic α(1→4)glucopyranose polymer, the polymer comprising:
   (i) a poly-α(1→4)glucopyranose portion comprising glucopyranose monomeric units; and
   (ii) a pendent group from the poly-α(1→4)glucopyranose portion comprising one or more hydrocarbon group(s) linked to a monomeric unit of the poly-α(1→4)glucopyranose portion via a linker segment comprising a silyl ether group.

2. The medical article of claim 1 wherein the pendent group is according to formula I:

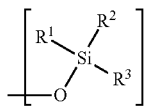

wherein one or more of $R^1$, $R^2$, and/or $R^3$ comprise a $C_1$-$C_{18}$ hydrocarbon group, with the proviso that the total number of carbon atoms among $R^1$, $R^2$, and $R^3$ is at three or more.

3. The medical article of claim 2, wherein the total number of carbon atoms among $R^1$, $R^2$, and $R^3$ is in the range of 6-12.

4. The medical article of claim 2, wherein two or more of $R^1$, $R^2$, and/or $R^3$ are selected from methyl and ethyl.

5. The medical article of claim 2, wherein one of $R^1$, $R^2$, or $R^3$ is a $C_4$-$C_{10}$ hydrocarbon group.

6. The medical article of claim 1 wherein the hydrophobic α(1→4)glucopyranose polymer has a degree of substitution in the range of 1.0 to 2.4 with the pendent groups.

7. The medical article of claim 1 wherein the hydrocarbon groups collectively represent a hydrophobic portion of the polymer, and the polymer has a weight ratio of the poly-α(1→4)glucopyranose portion to the hydrophobic portion in the range of 11:1 to 1:10.

8. The medical article of claim 1 wherein the polymer further comprises a second pendent group comprising a hydrocarbon group linked to the monomeric units of the poly-α(1→4)glucopyranose portion via a linker segment comprising a group that is not a silyl ether group.

9. The medical article of claim 8 wherein group that is not a silyl ether group is selected from the group consisting of ester, thioester, and carbonate.

10. The medical article of claim 8 wherein the second pendent group is pendent from the poly-α(1→4)glucopyranose portion at a degree of substitution less than the pendent group comprising the silyl ether group.

11. The medical article of claim 8 wherein the hydrophobic α(1→4)glucopyranose polymer has a degree of substitution in the range of 0.1 to 0.5 with the second pendent groups.

12. The implantable or injectable medical article of claim 1, wherein the polymeric matrix or composition comprises at least 50% of the hydrophobic α(1→4)glucopyranose polymer.

13. The implantable or injectable medical article of claim 1, wherein the polymeric matrix is in the form of a coating on an implantable medical device.

14. The implantable or injectable medical article of claim 1, wherein the polymeric matrix is in the form of a topcoat on an implantable medical device.

15. The implantable or injectable medical article of claim 1 which is in the form of an in situ formed droplet.

16. The implantable or injectable medical article of claim 1, wherein the polymeric matrix comprises the bioactive agent.

17. A method for treating a medical condition in a subject comprising a step of implanting or injecting a medical article in a subject, the article comprising a biodegradable polymeric matrix or composition comprising a hydrophobic α(1→4) glucopyranose polymer, the polymer comprising:
   (i) a poly-α(1→4)glucopyranose portion comprising glucopyranose monomeric units; and
   (ii) a pendent group from the poly-α(1→4)glucopyranose portion comprising one or more hydrocarbon group(s) linked to a monomeric unit of the poly-α(1→4)glucopyranose portion via a linker segment comprising a silyl ether group,
wherein the article (a) has a prosthetic, hemostatic, or anastomotic property useful for treating a medical condition at the site of implantation, (b) the article includes a bioactive agent which is released from the article and treats the medical condition, or (c) (a) and (b).

18. The medical article of claim 2, wherein one of $R^1$, $R^2$, or $R^3$ is a $C_3$-$C_8$ hydrocarbon group or a $C_4$-$C_{10}$ hydrocarbon group.

19. The medical article of claim 2, wherein one of $R^1$, $R^2$, or $R^3$ is an isopropyl or tert-butyl group.

20. The medical article of claim 2, wherein one of $R^1$, $R^2$, or $R^3$ is a decyl group.

21. An implantable or injectable medical article, the article comprising a bioactive agent releasable from the article and a biodegradable polymeric matrix or composition comprising a hydrophobic $\alpha(1\rightarrow4)$glucopyranose polymer, the polymer comprising:
  (i) a poly-$\alpha(1\rightarrow4)$glucopyranose portion comprising glucopyranose monomeric units; and
  (ii) a pendent group from the poly-$\alpha(1\rightarrow4)$glucopyranose portion comprising one or more hydrocarbon group(s) linked to a monomeric unit of the poly-$\alpha(1\rightarrow4)$glucopyranose portion via a hydrolytically cleavable linker segment comprising a silyl ether group.

22. The method of claim 17, where, following the step of implanting or injecting, the hydrophobic $\alpha(1\rightarrow4)$glucopyranose polymer has enhanced degradation via hydrolytic cleavage of the segment comprising a silyl ether group relative to a hydrophobic $\alpha(1\rightarrow4)$glucopyranose polymer that does not include the linker segment comprising a silyl ether group.

23. The method of claim 17 wherein the article that has a prosthetic, hemostatic, or anastomotic property is a vascular prosthesis, a wound dressing, a hemostatic barrier, a patch, or an anastomosis device.

\* \* \* \* \*